(12) United States Patent
Kawamura (10) Patent No.: US 9,947,101 B2
(45) Date of Patent: Apr. 17, 2018

(54) RADIOGRAPHIC IMAGE ANALYSIS DEVICE AND METHOD, AND RECORDING MEDIUM HAVING PROGRAM RECORDED THEREIN

(71) Applicant: FUJIFILM Corporation, Tokyo (JP)

(72) Inventor: Takahiro Kawamura, Ashigarakami-gun (JP)

(73) Assignee: FUJIFILM Corporation, Mintao-Ku, Tokyo (JP)

( * ) Notice: Subject to any disclaimer, the term of this patent is extended or adjusted under 35 U.S.C. 154(b) by 101 days.

(21) Appl. No.: 15/007,806

(22) Filed: Jan. 27, 2016

(65) Prior Publication Data

US 2016/0140721 A1  May 19, 2016

Related U.S. Application Data

(63) Continuation of application No. PCT/JP2014/003800, filed on Jul. 17, 2014.

(30) Foreign Application Priority Data

Jul. 31, 2013 (JP) .................................. 2013-159527
Nov. 6, 2013 (JP) .................................. 2013-229942

(51) Int. Cl.
 *G06K 9/00* (2006.01)
 *G06T 7/00* (2017.01)
 (Continued)

(52) U.S. Cl.
 CPC ............ *G06T 7/0075* (2013.01); *A61B 6/466* (2013.01); *A61B 6/5217* (2013.01); *A61B 6/544* (2013.01);
 (Continued)

(58) Field of Classification Search
 None
 See application file for complete search history.

(56) References Cited

U.S. PATENT DOCUMENTS

2008/0232668 A1* 9/2008 Kitamura .................. G06T 7/11
382/132

FOREIGN PATENT DOCUMENTS

JP      10-057361 A    3/1998
JP    2008-011894 A    1/2008
(Continued)

OTHER PUBLICATIONS

Machine translation of 2010-005032.*
(Continued)

*Primary Examiner* — Hadi Akhavannik
(74) *Attorney, Agent, or Firm* — Sughrue Mion, PLLC (57) ABSTRACT

A subject image is acquired. Model information, in which a model image captured by irradiating each of a plurality of models different from the subject with radiation is associated with a body thickness distribution of the model in the model image is acquired for each of the plurality of models. Characteristic information indicating characteristics of the subject image is acquired. Characteristic information indicating the characteristics of each of the plurality of model images is acquired, on the basis of the plurality of model information items. The model image having characteristic information similar to the characteristic information of the subject image is specified. The body thickness distribution associated with the specified model image is determined as the body thickness distribution of the subject image.

12 Claims, 5 Drawing Sheets

(51) Int. Cl.
*A61B 6/00* (2006.01)
*G06T 7/62* (2017.01)
*A61B 6/03* (2006.01)

(52) U.S. Cl.
CPC ............... *G06T 7/62* (2017.01); *A61B 6/032* (2013.01); *G06T 2207/10072* (2013.01); *G06T 2207/10116* (2013.01); *G06T 2207/30061* (2013.01)

(56) References Cited

FOREIGN PATENT DOCUMENTS

| | | |
|---|---|---|
| JP | 2010-005032 A | 1/2010 |
| JP | 2011-135990 A | 7/2011 |
| JP | 2012-020009 A | 2/2012 |
| WO | 2007/114470 A1 | 10/2007 |

OTHER PUBLICATIONS

Written Opinion of International Searching Authority of PCT/JP2014/003800 dated Oct. 7, 2014.
International Search Report of PCT/JP2014/003800 dated Oct. 7, 2014.
Communication dated Aug. 2, 2016, from the Japanese Patent Office in counterpart application No. 2013-229942.

\* cited by examiner

RADIOGRAPHIC IMAGE ANALYSIS DEVICE AND METHOD, AND RECORDING MEDIUM HAVING PROGRAM RECORDED THEREIN

CROSS REFERENCE TO RELATED APPLICATIONS

The present application is a Continuation of PCT International Application No. PCT/JP2014/003800 filed on Jul. 17, 2014, which claims priority under 35 U.S.C. § 119(a) to Japanese Patent Application No. 2013-159527 filed on Jul. 31, 2013 and Japanese Patent Application No. 2013-229942 filed on Nov. 6, 2013. Each of the above applications is hereby expressly incorporated by reference, in its entirety, into the present application.

BACKGROUND OF THE INVENTION

1. Field of the Invention

The present invention relates to an image analysis device and method and a recording medium having a program which analyze a captured radiographic image of a subject.

2. Description of the Related Art

When a radiographic image of a subject is captured by radiation passing through the subject, the influence of the scattering of radiation or a reduction in the transmissivity of radiation in the subject increases as the thickness of the subject increases, which results in a change in the quality of the acquired radiographic image.

In order to respond to the above-mentioned problem, a technique has been proposed which roughly estimates the thickness of the subject, on the basis of various kinds of information, such as imaging conditions, a signal value of a radiographic image, the histogram width of the signal value of the radiographic image, and the length of the subject in the subject image in a predetermined direction, and changes the conditions of image processing, such as a process of removing scattered X-rays of the captured radiographic image, or the imaging conditions applied to the capture of the radiographic image, on the basis of the estimated thickness of the subject.

For example, WO2007/114470A discloses a technique which generates a simulation image for determining appropriate imaging conditions corresponding to the thickness data of the human body and uses a representative thickness of an imaging target part which is measured from a computed tomography image (CT image) as the body thickness of the subject.

SUMMARY OF THE INVENTION

It is preferable to accurately acquire the body thickness of the subject in order to further increase the effect of determining the image processing conditions or the imaging conditions on the basis of the body thickness of the subject and improving image quality. However, as in the method described in WO2007/114470A, when the body thickness of the subject is represented by one representative value, it is difficult to change the image processing conditions or the imaging conditions which can sufficiently suppress a change in the image quality of the subject depending on the differences in the body thickness at each position of the subject.

The invention has been made in view of the above-mentioned problems and an object of the invention is to perform an image analysis process which analyzes a radiographic image captured by irradiating a subject with radiation to accurately estimate a body thickness distribution of the subject.

According to an aspect of the invention, there is provided a radiographic image analysis device that analyzes a subject image captured by irradiating a subject with radiation to estimate a body thickness distribution of the subject. The radiographic image analysis device includes: an image acquisition unit that acquires the subject image; a model information acquisition unit that acquires model information, in which a model image captured by irradiating each of a plurality of models different from the subject with radiation is associated with a body thickness distribution of the model in the model image, for each of the plurality of models; and a body thickness distribution determination unit that acquires characteristic information indicating characteristics of the subject image, acquires characteristic information indicating the characteristics of each of the plurality of model images, on the basis of the plurality of model information items, specifies the model image having characteristic information similar to the characteristic information of the subject image, and determines the body thickness distribution associated with the specified model image as the body thickness distribution of the subject image.

According to another aspect of the invention, there is provided a radiographic image analysis method that is performed in a radiographic image analysis device and analyzes a subject image captured by irradiating a subject with radiation to estimate a body thickness distribution of the subject. The radiographic image analysis method includes: an image acquisition step of acquiring the subject image; a model information acquisition step of acquiring model information, in which a model image captured by irradiating each of a plurality of models different from the subject with radiation is associated with a body thickness distribution of the model in the model image, for each of the plurality of models; and a body thickness distribution determination step of acquiring characteristic information indicating characteristics of the subject image, acquiring characteristic information indicating the characteristics of each of the plurality of model images, on the basis of the plurality of model information items, specifying the model image having characteristic information similar to the characteristic information of the subject image, and determining the body thickness distribution associated with the specified model image as the body thickness distribution of the subject image.

In addition, a program may be provided which causes a computer to perform the radiographic image analysis method according to the above-mentioned aspect of the invention.

The "body thickness" means the sum of the thicknesses of subject regions other than an air region on an emitted radiation path. In addition, the body thickness distribution indicates the thickness distribution of the subject at each position on a two-dimensional radiographic image.

The "characteristic information" may be defined from any point of view as long as it indicates the characteristics of the radiographic image. For example, the characteristic information can be one or more information items selected from information about an imaging target, information about imaging conditions when an image is captured, grid information indicating whether a scattered X-ray removal grid is present and the type of scattered X-ray removal grid, or any combination thereof. In addition, the characteristic information may be information indicating one characteristic of the radiographic image or information indicating a plurality of characteristics of the radiographic image. Furthermore, in the characteristic information, each characteristic may be defined by any method. For example, each characteristic may be defined by one parameter or a plurality of parameters.

In the radiographic image analysis device according to the above-mentioned aspect of the invention, it is preferable that the characteristic information is imaging target information indicating physical characteristics of an imaging target.

The "imaging target information" may be specified by any method as long as it indicates the physical characteristics of the imaging target such as the shape or size of the skeletal structure, the amount of muscle, and the amount of fat of the imaging target. For example, the following may be used: the histogram width of the signal value of the radiographic image (the difference between the maximum value and the minimum value of the histogram of the signal value); the representative length (for example, the width of the abdomen) of a predetermined part of the subject in the radiographic image; and the height, weight, sex, and age (an adult or a child) of the subject. In addition, one or more imaging target information items may be provided.

In the above-mentioned case, preferably, the radiographic image analysis device further includes a position alignment unit that aligns the subject image and the model image such that the corresponding positions of the subject image and the model image are aligned with each other. Preferably, the body thickness distribution determination unit acquires the characteristic information from the subject image and the model image which are aligned with each other and specifies the model image having characteristic information similar to the characteristic information of the subject image.

In the above-mentioned case, preferably, the image acquisition unit further acquires grid information including information indicating whether or not a scattered X-ray removal grid is used to capture the subject image and the type of scattered X-ray removal grid when the scattered X-ray removal grid is used to capture the subject image. Preferably, the model information acquisition unit further acquires the grid information of the model image. Preferably, the body thickness distribution determination unit acquires the characteristic information from the subject image and the model image included in the model information having grid information identical to the grid information of the subject image and specifies the model image having characteristic information similar to the characteristic information of the subject image.

The "information indicating the type of grid" can include at least one of a grid ratio, grid density, information indicating whether the grid is a convergence type or a parallel type, a focusing distance when the grid is a convergence type, and an interspace material (for example, aluminum, fiber, or Bakelite).

In the radiographic image analysis device according to the above-mentioned aspect of the invention, the subject image may be captured without using the scattered X-ray removal grid. In this case, it is preferable that the model image is captured without using the scattered X-ray removal grid.

In the invention, preferably, the body thickness distribution of the model image is created by acquiring a three-dimensional image of the model obtained by three-dimensional imaging and measuring a body thickness on a straight line corresponding to a radiation path of the model image at each position of the acquired three-dimensional image.

Preferably, the image acquisition unit further acquires part information indicating an imaging target part of the subject image. Preferably, the model information acquisition unit further acquires the part information of the model image. Preferably, the body thickness distribution determination unit acquires the characteristic information from the subject image and the model image included in the model information having part information identical to the part information of the subject image and specifies the model image having characteristic information similar to the characteristic information of the subject image.

According to the invention, a subject image is acquired. Model information, in which a model image captured by irradiating each of a plurality of models different from a subject with radiation is associated with a body thickness distribution of the model in the model image, is acquired for each of the plurality of models. Characteristic information indicating the characteristics of the subject image is acquired. Characteristic information indicating the characteristics of each of the plurality of model images is acquired, on the basis of the plurality of model information items. The model image having characteristic information similar to the characteristic information of the subject image is specified. The body thickness distribution associated with the specified model image is determined as the body thickness distribution of the subject image. Therefore, among the body thickness distributions of a plurality of models, the body thickness distribution of the model image having similar characteristics to the subject image can be determined as the body thickness distribution of the subject image. As a result, it is possible to accurately determine the body thickness distribution of the subject image.

DESCRIPTION OF THE PREFERRED EMBODIMENTS

Figure 1:
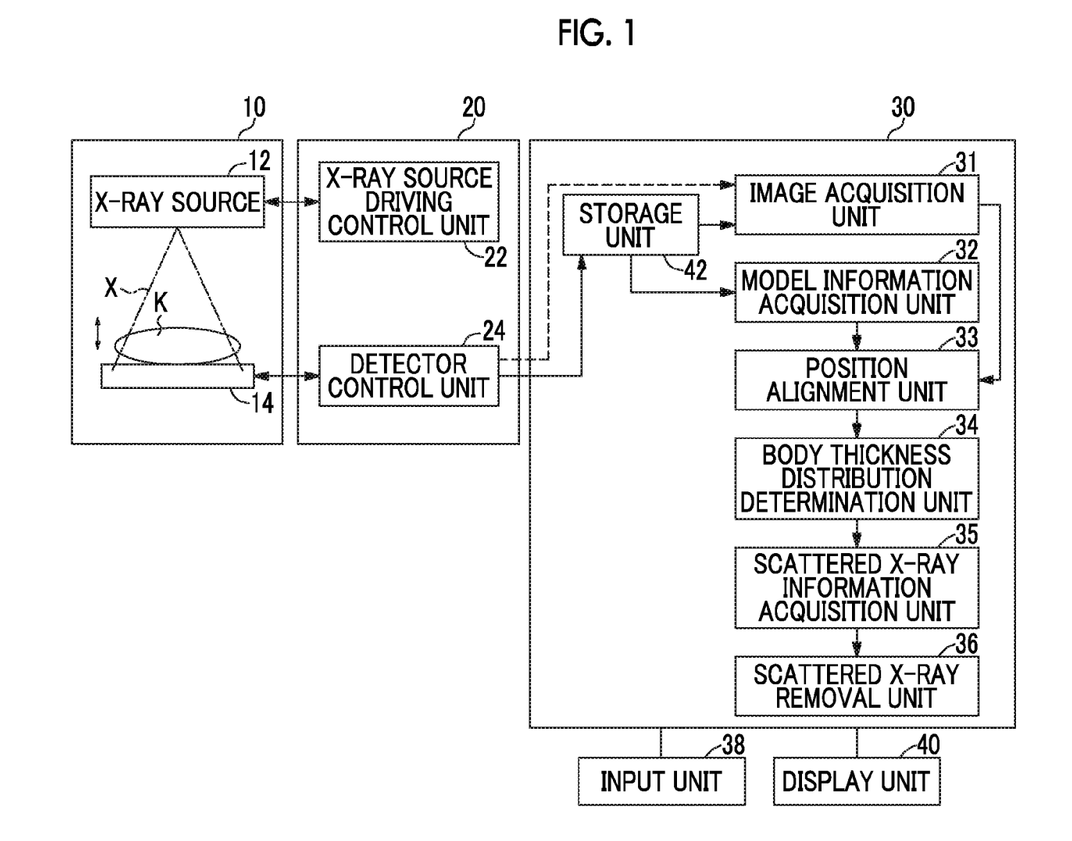
FIG. 1 is a block diagram schematically illustrating the structure of a radiography system to which a radiographic image analysis device according to a first embodiment of the invention is applied.

Hereinafter, embodiments of the invention will be described with reference to the drawings. FIG. 1 is a block diagram schematically illustrating the structure of a radiography system to which a radiographic image analysis device according to a first embodiment of the invention is applied. As illustrated in FIG. 1, the radiography system according to this embodiment includes an imaging device 10, a control device 20 which controls the system, and an image analysis device 30 (radiographic image analysis device).

The imaging device 10 includes an X-ray source 12 which irradiates a subject K with X-rays and a radiation detector 14 which detects X-rays passing through the subject K and acquires a radiographic image of the subject K. In this embodiment, a scattered X-ray removal grid (grid) for removing scattered X-rays which are scattered by the subject K among the X-rays passing through the subject K is not provided between the subject K and the radiation detector 14.

The control device 20 includes an X-ray source driving control unit 22 which controls the driving of the X-ray source 12 according to set radiography conditions and a detector control unit 24 which controls the radiation detector 14 such that the radiographic image (subject image) of the subject is acquired and stores the radiographic image in a storage unit 42.

The image analysis device 30 includes an image acquisition unit 31 which acquires a captured subject image Ik of the subject K from, for example, the detector control unit 24 or the storage unit 42, which will be described below, a model information acquisition unit 32 which acquires model information Cmi, in which model images Imi captured by irradiating a plurality of models Mi ($1 \leq i \leq n$: n is an integer equal to or greater than 1) different from the subject K with radiation are associated with body thickness distributions Tmi(x, y) of the models Mi in the model images Imi, for the plurality of models Mi, a position alignment unit 33 which aligns the corresponding positions of the subject image Ik and the model image Imi, a body thickness distribution determination unit 34 which acquires characteristic information indicating the characteristics of the subject image Ik, acquires characteristic information indicating the characteristics of the plurality of model images Imi on the basis of a plurality of model information items, specifies the model image Imi having characteristic information similar to the characteristic information of the subject image Ik, and determines the body thickness distribution Tmi(x, y) associated with the specified model image Imi as a body thickness distribution Tk(x, y) of the subject image, a scattered X-ray information acquisition unit 35 which acquires scattered component information indicating a scattered component of the X-ray included in the subject image Ik on the basis of the determined body thickness distribution Tk(x, y), a scattered X-ray removal unit 36 which performs a process of removing a scattered X-ray from the radiographic image acquired by the radiation detector 14 on the basis of the scattered component information acquired by the scattered X-ray information acquisition unit 35, an input unit 38, a display unit 40, and the storage unit 42 which includes storage media, such as a memory and a hard disk, and stores various kinds of information. The input unit 38 receives various inputs of the operator to the image analysis device 30. Specifically, the input unit 38 is, for example, a keyboard, a mouse, or a touch panel. The display unit 40 is, for example, a CRT display or a liquid crystal display and assists the input of the radiographic image acquired by the imaging device 10 and various inputs required for a scattered X-ray removal process which will be described below.

The image acquisition unit 31, the model information acquisition unit 32, the position alignment unit 33, the body thickness distribution determination unit 34, the scattered X-ray information acquisition unit 35, the scattered X-ray removal unit 36, the input unit 38, the display unit 40, and the storage unit 42 can be formed by a computer system such as a general personal computer.

The image analysis device 30 analyzes the subject image Ik which has been captured by irradiating the chest and abdomen of the subject K, who is the person to be examined, with radiation to estimate the body thickness distribution Tk of the subject K.

The subject image Ik acquired by the detector control unit 24 is stored in the storage unit 42 of the image analysis device 30. In addition, the model information Cmi ($1 \leq i \leq n$) in which a plurality of model images Imi ($1 \leq i \leq n$), which are the radiographic images of the chest and abdomen of the models Mi ($1 \leq i \leq n$) different from the subject K obtained by radiography, are associated with the body thickness distribution Tmi ($1 \leq i \leq n$) of the model Mi which is the subject of the model image Imi ($1 \leq i \leq n$) is created in advance and is then stored in the storage unit 42. In addition, the storage unit 42 also stores a three-dimensional CT image Vmi having the model Mi as the subject and various kinds of information required for the scattered X-ray removal process. It is assumed that the plurality of models Mi ($1 \leq i \leq n$) include persons of various physiques, sexes, and ages. In this embodiment, it is assumed that the subject image Ik and the model images Imi ($1 \leq i \leq n$) included in each model information item Cmi ($1 \leq i \leq n$) are captured without using a grid.

The body thickness distribution Tmi(x, y) ($1 \leq i \leq n$) is created in advance on the basis of the three-dimensional CT image Vmi ($1 \leq i \leq n$) of the model Mi which is the subject of the model image Imi. In the specification, the body thickness means the sum of the thicknesses of subject regions except for an air region on the path of the emitted radiation.

Figure 2:
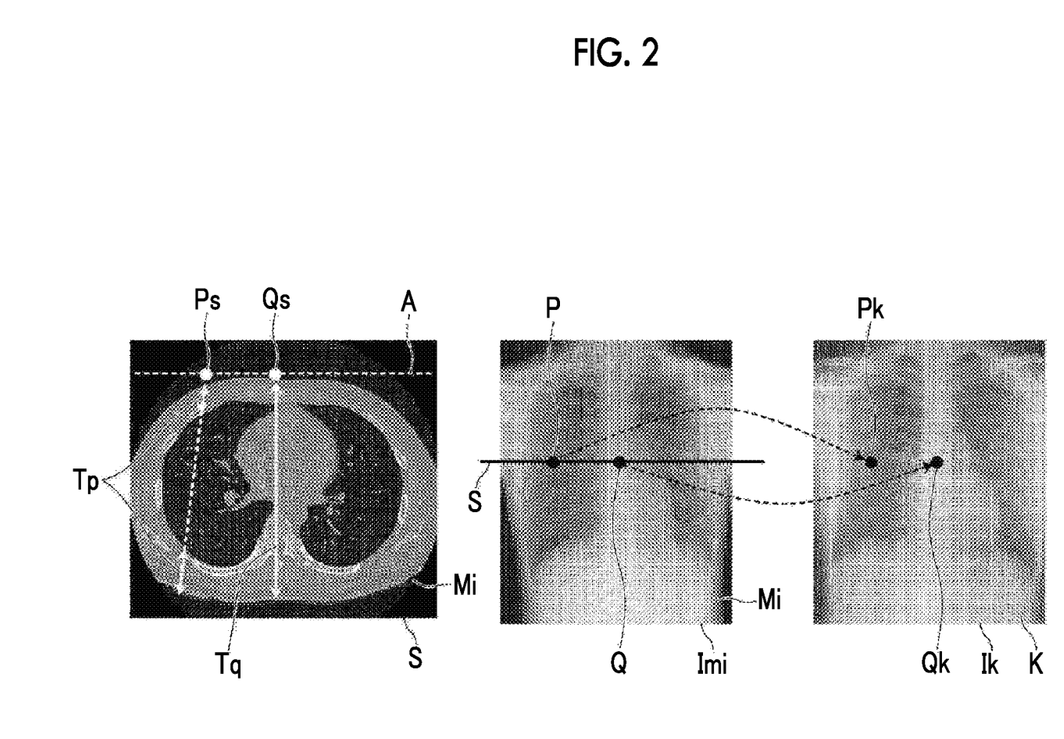
FIG. 2 is a diagram illustrating a method for measuring a body thickness distribution of a model image and a correspondence relationship between the body thickness distributions of the model image and a subject image.

FIG. 2 is a diagram illustrating a method for measuring the body thickness distribution of the model image Imi and a correspondence relationship between the body thickness distribution of the model image Imi and the body thickness distribution of the subject image Ik. An example of the method for measuring the body thickness at coordinate points P and Q on the model image Imi will be described with reference to FIG. 2. An example of the model image Imi which is a two-dimensional radiographic image of the model Mi is illustrated at the center of FIG. 2. An example of a tomographic image S which is generated from the three-dimensional image Vmi of the model Mi is illustrated on the left side of FIG. 2. An example of the subject image Ik is illustrated on the right side of FIG. 2. In FIG. 2, the tomographic image S indicates a tomographic image including the path of radiation passing through coordinate points Ps and Qs on the three-dimensional image Vmi which correspond to the coordinate points P and Q on the model image Imi and a line A in the tomographic image S indicates a projection plane of the tomographic image S corresponding to the model image Imi. As illustrated in FIG. 2, the body thicknesses corresponding to the coordinate points P and Q on the model image Imi are obtained by measuring body thicknesses Tp and Tq on the path of the radiation, which passes through the coordinate points Ps and Qs on the tomographic image 5, on the tomographic image S. For example, for the body thickness Tp illustrated in FIG. 2, since a plurality of air portions are present in the lung field on the path, the distance of an air region is not converted into the body thickness and the sum of the body thicknesses is 72 mm. In addition, for the body thickness Tq corresponding to the coordinate point Q, since a small air region is present on the path, the sum of the body thicknesses is 221 mm.

Next, a method for creating the body thickness distribution Tmi(x, y) ($1 \leq i \leq n$) will be described. First, the image analysis device 30 acquires the three-dimensional CT image Vmi and the model image Imi having the model Mi as the subject from the storage unit 42. Then, the image analysis device 30 relatively enlarges and moves the coordinate systems of the model image Imi and the three-dimensional CT image Vmi to align the model image Imi and the three-dimensional CT image at corresponding positions. In addition, the image analysis device 30 calculates the projection plane of the three-dimensional CT image Vmi which corresponds to the model image Imi and a straight line (virtual radiation path) of the three-dimensional CT image Vmi which corresponds to the passage path of radiation with respect to the model image Imi. Then, the image analysis device 30 specifies coordinates (x1, y1, z1) in the three-dimensional CT image Vmi which correspond to the coordinates (x1, y1) of one pixel of the model image Imi in the projection plane and measures the thickness (body thickness) of the subject located on the virtual path of radiation passing through the coordinates (x1, y1, z1). Then, the image analysis device 30 registers the measured body thickness as a body thickness Tmi(x1, y1) at the coordinates (x1, y1). Similarly, the image analysis device 30 repeatedly performs the process of measuring the body thickness corresponding to the coordinates of each pixel on the model image Imi and registering the measured body thickness as the body thickness corresponding to each coordinate point for the coordinates of all the other pixels on the model image Imi to create the body thickness distribution Tmi(x, y) of the model image Imi.

Next, the flow of a radiographic image analysis process performed by the image analysis device 30 according to this embodiment will be described with reference to FIG. 2. Hereinafter, in some cases, the body thickness distribution Tmi(x, y) is referred to as a body thickness distribution Tmi and the body thickness distribution Tk(x, y) is referred to as a body thickness distribution Tk. In addition, the model image Imi (1<i<n), the model information Cmi (1<i<n), and the model Mi (1<i<n) are referred to as a model image Imi, model information Cmi, and a model Mi, respectively.

Figure 3:
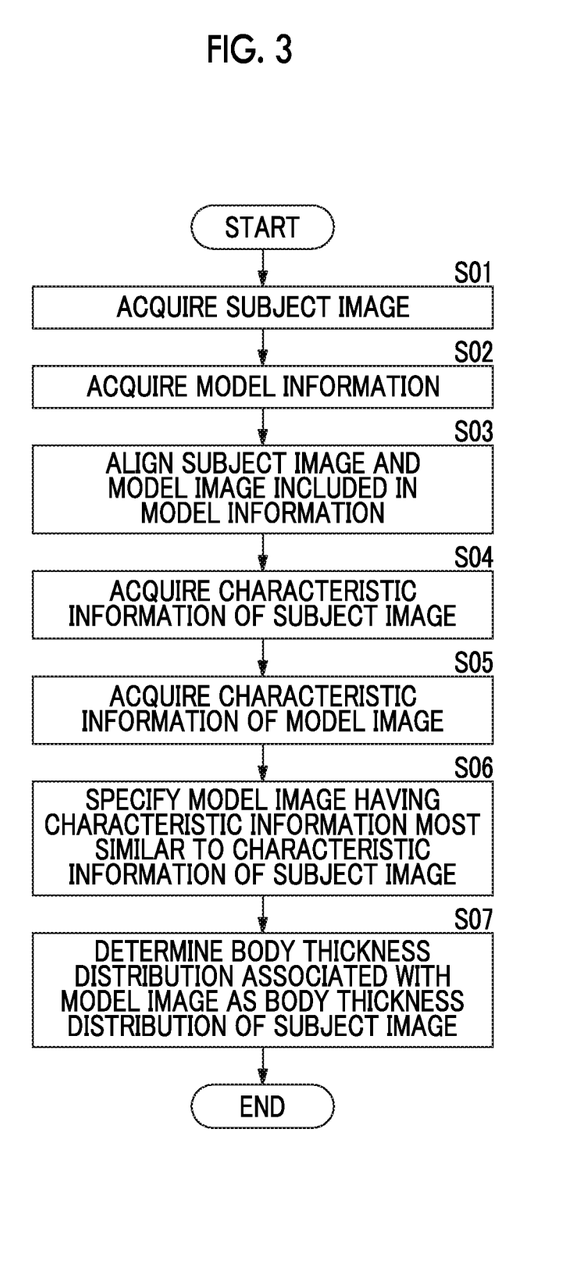
FIG. 3 is a flowchart illustrating a process performed in the first embodiment.

First, the image acquisition unit 31 acquires the subject image Ik obtained by performing radiography on the chest and abdomen of a patient, who is the subject K, from the storage unit 42 (S01).

Then, the model information acquisition unit 32 acquires each of the plurality of model information items Cmi (S02). The order of the process of acquiring the subject image Ik (S01) and the process of acquiring the model information Cmi (S02) may be reversed or the processes may be performed at the same time.

The position alignment unit 33 appropriately enlarges and moves the plurality of model images Imi such that the corresponding positions of the subject image Ik and the plurality of model images Imi are aligned with each other to align the subject image Ik and the plurality of model images Imi (S03).

Any known method may be used to align the subject image Ik and the plurality of model images Imi. For example, it is preferable to perform the alignment using an image obtained by extracting a low-frequency component from the subject image Ik and an image obtained by extracting a low-frequency component from the model image Imi. In this case, the low-frequency components obtained by removing a high-frequency component including information about a detailed part, such as the blood vessel, are aligned to align the positions of rough targets, such as bones or organs. Therefore, it is possible to accurately perform alignment.

Then, the body thickness distribution determination unit 34 acquires the characteristic information from the aligned subject image Ik (S04). Similarly, the body thickness distribution determination unit 34 acquires the characteristic information from the plurality of model images Imi (S05). The order of the process of acquiring the characteristic information from the subject image Ik (S04) and the process of acquiring the characteristic information from the model images Imi (S05) may be reversed or the processes may be performed at the same time.

The characteristic information may be defined from any point of view as long as it indicates the characteristics of the radiographic image. For example, the characteristic information can be one or more information items selected from information about an imaging target, information about imaging conditions when an image is captured, and information indicating whether a scattered X-ray removal grid is present and the type of scattered X-ray removal grid, or any combination thereof. In addition, the characteristic information may be information indicating one characteristic of the radiographic image or information indicating a plurality of characteristics of the radiographic image. Furthermore, in the characteristic information, each characteristic may be defined by any method. For example, each characteristic may be defined by one parameter or a plurality of parameters.

In this embodiment, the body thickness distribution determination unit 34 extracts, as the characteristic information, the difference (histogram width) between the maximum value and the minimum value of the signal value of the radiographic image which is imaging target information indicating the physical characteristics of an imaging target (subject) from the subject image Ik and the plurality of model images Imi.

The imaging target information may be specified by any method as long as it indicates the physical characteristics of the imaging target such as the shape or size of the skeletal structure, the amount of muscle, and the amount of fat of the imaging target. For example, the following may be used: the histogram width of the signal value of the radiographic image (the difference between the maximum value and the minimum value of the histogram of the signal value); the representative length (for example, the width of the abdomen) of a predetermined part of the subject in the radiographic image; and the height, weight, sex, and age (an adult or a child) of the subject. In addition, one or more imaging target information items may be used. The imaging target information may be acquired by any method. For example, the imaging target information may be extracted and acquired from the supplementary information of the image, may be extracted and acquired from the image by a known image recognition process, or may be acquired from the user.

Then, the body thickness distribution determination unit 34 compares the histogram widths of the signal values of the subject image Ik and the plurality of model images Imi and specifies a model image Imo with a histogram width closest to the histogram width of the subject image Ik (S06). In the radiographic image, as the size of the subject becomes larger, the distribution of the signal value tends to become wider. Therefore, when the histogram width of the signal value is used as the imaging target information, it is possible to specify the model image Imo in which the model Mo having a similar physique to the subject K of the subject image Ik is the subject.

Then, the body thickness distribution determination unit 34 determines a body thickness distribution Tmo associated with the specified model image Imo as the body thickness distribution Tk of the subject image Ik and ends the radiographic image analysis process according to the first embodiment (S07). As a result, for example, the body thicknesses Tp and Tq at the coordinate points P and Q in the model image Imi illustrated at the center of FIG. 2 are determined as the body thicknesses at the corresponding coordinate points Pk and Qk in the subject image Ik illustrated on the right side of FIG. 2.

In this embodiment, when an instruction to perform the scattered X-ray removal process for the subject image Ik is received from the user after the body thickness distribution determination process (S07) illustrated in FIG. 3, a scattered X-ray information acquisition process and the scattered X-ray removal process are performed as the optional functions of the image analysis device 30. First, the scattered X-ray information acquisition unit 35 acquires the subject image Ik and the body thickness distribution Tk(x, y) of the subject image Ik and calculates a primary X-ray image Ip(x, y) and a scattered X-ray image Is(x, y) on the basis of the following Expressions (1) and (2).

$$Ip(x,y)=Ik(x,y)\times\exp(-\mu\times Tk(x,y)) \quad (1)$$

$$Is(x,y)=Ik(x,y)*P(Tk(x,y)) \quad (2)$$

Here, (x, y) is the coordinates of a pixel position of the subject image Ik, Ip(x, y) is a primary X-ray image at the pixel position (x, y), Is(x, y) is a scattered X-ray image at the pixel position (x, y), Ik(x, y) is an incident dose at the pixel position (x, y), $\mu$, is a linear attenuation coefficient of the subject, and P(Tk(x, y)) is a convolution kernel indicating a point spread function corresponding to the thickness of the subject at the pixel position (x, y). Expression (1) is based on a known exponential attenuation law. It is assumed that scattered X-ray information associated with the point spread function of a scattered X-ray which is acquired for each of a plurality of body thicknesses is created in advance by measurement and is then stored in the storage unit 42. For the detailed description of the point spread function, it is possible to refer to, for example, the description in JP1998-57361A (JP-H10-57361A).

Then, the scattered X-ray removal unit 36 subtracts the scattered X-ray image Is(x, y) from the subject image Ik(x, y) to generate a processed image from which the influence of scattered X-rays has been removed and stores the processed image in the storage unit 42. The processed image is appropriately displayed on the display unit 40 in response to an instruction from the user.

According to this embodiment, among the body thickness distributions of a plurality of models, the body thickness distribution of the model image Imo having similar characteristics to the subject image Ik can be determined as the body thickness distribution of the subject image Ik. Therefore, it is possible to accurately determine the body thickness distribution of the subject image Ik. Since the body thickness distribution Tk is used to remove the scattered X-rays, it is possible to accurately perform a process of removing the scattered X-rays of the subject image Ik and to improve the quality of the processed image, such as the contrast of the processed image.

As described in this embodiment, when the imaging target information indicating the physical characteristics of the subject is used as the characteristic information, it is possible to determine the body thickness distribution of the model Mi with a similar physique as the body thickness distribution Tk of the subject image Ik. Therefore, it is possible to accurately calculate the body thickness distribution Tk.

In the above-described embodiment, the image analysis device 30 includes the position alignment unit 33, aligns the subject image Ik and the plurality of model images Imi, acquires the characteristic information from the subject image Ik, and acquires the characteristic information from the plurality of model images Imi. In this case, it is possible to reduce the influence of the positional deviation between the subject image Ik and the subject in the plurality of model images Imi and to compare the characteristic information of the subject image Ik with the characteristic information of the plurality of model images Imi. Therefore, it is possible to accurately determine the model image Imo having similar characteristic information to the subject image Ik. In addition, since the determined model image Imo and the subject image Ik are aligned with each other, it is possible to appropriately reflect the body thickness distribution of the model image Imo in the body thickness distribution of the subject image Ik at each position.

When one of the subject image Ik and the model image Imi is captured using a grid and the other image is captured without using a grid, the amount of scattered X-rays generated from the subject image Ik is different from the amount of scattered X-rays generated from the plurality of model images Imi, which makes it difficult to accurately compare the characteristic information of the subject image Ik with the characteristic information of the model image Imi. For this reason, as in the above-described embodiment, both the subject image Ik and the plurality of model images Imi are captured without using a grid. Therefore, the amounts of scattered X-rays included in the two images can be close to each other and it is possible to accurately determine the similarity between the characteristic information of the subject image Ik and the characteristic information of the model images Imi.

In the above-described embodiment, the body thickness distributions of the plurality of model images Imi are created by capturing the three-dimensional image of the model Mi to acquire the three-dimensional image Vmi and measuring the body thickness on a straight line corresponding to the radiation path of the model image Imi at each position of the acquired three-dimensional image Vmi. Therefore, it is possible to accurately obtain the body thickness distribution Tmi corresponding to each model image Imi. In addition, various types of three-dimensional images can be applied as the three-dimensional image. However, it is most preferable to use a three-dimensional CT image in order to determine the thickness of the subject on the basis of the signal value obtained by radiography.

Figure 4:
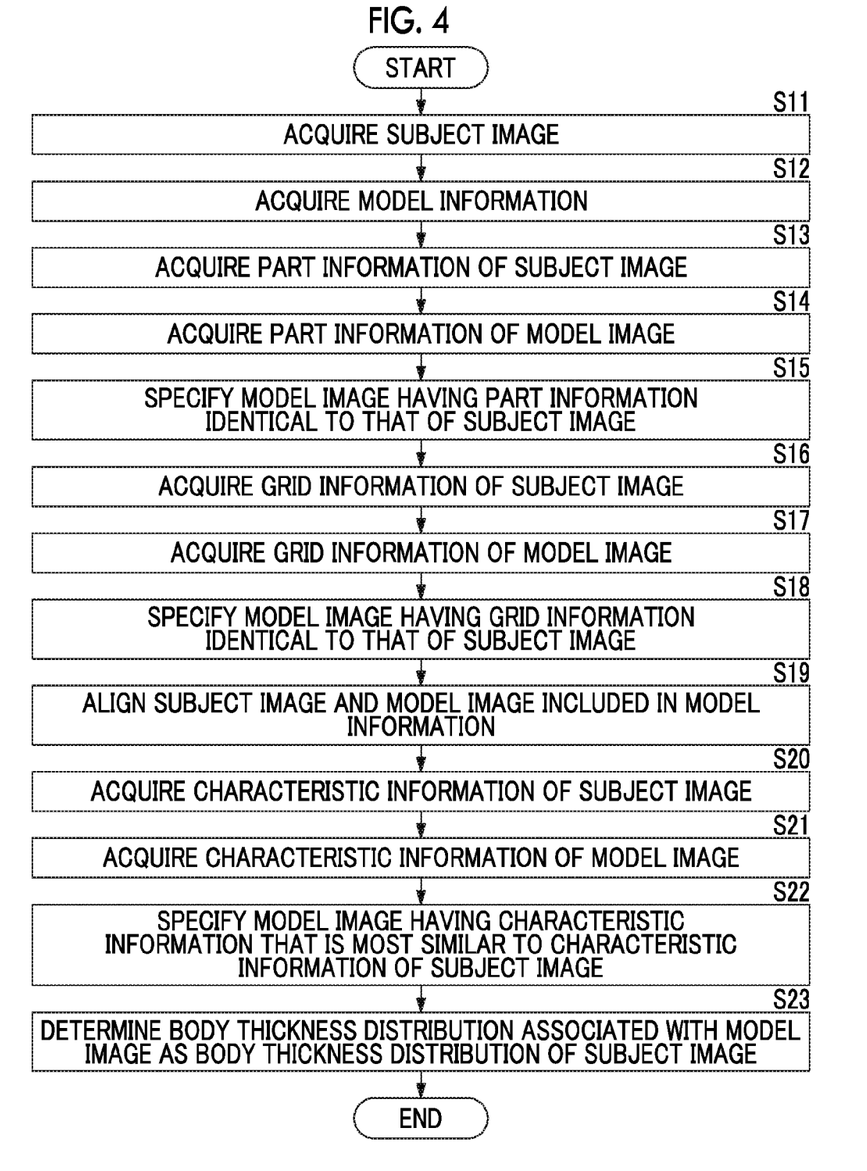
FIG. 4 is a flowchart illustrating a process performed in a second embodiment.

Next, a second embodiment will be described. FIG. 4 is a flowchart illustrating the flow of a process according to the second embodiment. The second embodiment differs from the first embodiment in that the image acquisition unit 31 further acquires grid information of the subject image Ik, the model information acquisition unit 32 further acquires grid information of a plurality of model images Imi, and the body thickness distribution determination unit 34 acquires characteristic information from the model images Imi included in the model information Cmi having grid information identical to the grid information of the subject image Ik. In addition, the second embodiment differs from the first embodiment in that the image acquisition unit 31 further acquires part information indicating an imaging target part of the subject image Ik, the model information acquisition unit 32 further acquires part information of the model image Imi, and the body thickness distribution determination unit 34 acquires characteristic information from the model images Imi included in the model information Cmi having part information identical to the part information of the subject image Ik. In the second embodiment, the functions and processes of the other components are substantially the same as those in the first embodiment. Therefore, the description is focused on the difference from the first embodiment and the description of the same portions will not be repeated.

In the second embodiment, it is assumed that the supplementary information of the subject image Ik and the supplementary information of the plurality of model images Imi include part information and grid information. It is assumed that the model images Imi included in a plurality of model information items Cmi include a plurality of model images which are captured without using a grid and a plurality of model images which are captured using plural types of grids. In addition, it is assumed that the model images Imi included in the plurality of model information items Cmi include the model images in which an imaging part is any one of the head, the chest, and the abdomen.

The grid information includes at least information indicating whether a grid is used to capture an image and includes information indicating the type of grid when a grid is used. The information indicating the type of grid can include at least one of a grid ratio, grid density, information indicating whether the grid is a convergence type or a parallel type, a focusing distance when the grid is a convergence type, and an interspace material (for example, aluminum, fiber, or Bakelite). The grid information may be acquired by any method. For example, it is considered that the grid information is extracted from the input of the user or the supplementary information of the image. Here, the grid information includes information indicating whether a grid is used to capture an image and information indicating the type of grid when a grid is used to capture an image.

The part information includes information about an imaging target part, such as the head, the chest, or the abdomen. The part information may be indirectly specified by, for example, the organ included in the part. In addition, the part information includes information about the imaging direction of each part or the posture of the subject. The part information may be acquired by any method. For example, the part information may be acquired from the header information of the image or the input information of the user. In addition, an organ recognition process may be performed for the image to determine a part from the organ included in the image and then the part information may be acquired.

First, in the second embodiment, the image acquisition unit 31 acquires the subject image Ik (S11) and the model information acquisition unit 32 acquires the plurality of model information items Cmi (S12). In addition, S11 and S12 correspond to S01 and S02, respectively.

Then, the image acquisition unit 31 acquires the part information of the subject image Ik from the supplementary information of the subject image Ik (S13). The model information acquisition unit 32 acquires the part information from the supplementary information of each of the plurality of model images Imi (S14). The order of the process of acquiring the part information of the subject image Ik (S13) and the process of acquiring the part information of the plurality of model images Imi (S14) may be reversed or the processes may be performed at the same time.

Then, the body thickness distribution determination unit 34 specifies only the model images Imi, which are included in the model information Cmi having part information identical to the part information of the subject image Ik, among the plurality of model images Imi (S15).

Then, the image acquisition unit 31 acquires the grid information of the subject image Ik from the supplementary information of the subject image Ik (S16). The model information acquisition unit 32 acquires the grid information from the supplementary information of each of the plurality of model images Imi (S17). The order of the process of acquiring the grid information of the subject image Ik (S16) and the process of acquiring the grid information of the plurality of model images Imi (S17) may be reversed or the processes may be performed at the same time.

Then, the body thickness distribution determination unit 34 further specifies the model image Imi, which is included in the model information Cmi having grid information identical to the grid information of the subject image Ik, among the plurality of model images Imi specified in S15 (S18).

Then, the position alignment unit 33 aligns the model image Imi specified in S18, that is, one or more model images Imi having the same grid information and part information as the subject image Ik, with the subject image Ik (S19).

Then, similarly to the first embodiment, the body thickness distribution determination unit 34 acquires characteristic information from the aligned subject image Ik (S20), acquires characteristic information from the model images Imi (S21), specifies the model image Imo having the characteristic information that is most similar to the characteristic information of the subject image (S22), determines a body thickness distribution Tmo corresponding to the specified model image Imo as the body thickness distribution Tk of the subject image Ik, and ends the radiographic image analysis process according to the second embodiment (S23). In addition, S20 to S23 correspond to S04 to S07 in the first embodiment, respectively.

In the second embodiment, the characteristics associated with the model images Imi having grid information identical to the grid information of the subject image Ik are acquired, the model image Imo having characteristic information similar to the characteristic information of the subject image Ik is specified, and the body thickness distribution Tmo corresponding to the specified model image is determined as the body thickness distribution Tk of the subject image Ik. In this case, since the grid information of the subject image Ik is identical to the grid information of the plurality of model images Imi, the influence of the amount of scattered X-rays generated due to the difference between the grid information items is reduced and it is possible to accurately extract the characteristics of both images. Therefore, it is possible to accurately extract the model image Imo having similar characteristics to the subject image Ik and to accurately determine the body thickness distribution.

In the second embodiment, the characteristic information items of the model images Imi having part information identical to the part information of the subject image Ik are compared with each other, the model image Imo having characteristic information similar to the characteristic information of the subject image Ik is specified, and the body thickness distribution Tmo corresponding to the specified model image Imo is determined as the body thickness distribution Tk of the subject image Ik. In this case, since the part information of the subject image Ik is identical to the part information of the plurality of model images Imi, the influence of, for example, the difference between the amounts of scattered X-rays generated due to the difference between the parts is reduced and it is possible to accurately extract the characteristics of both images. Therefore, it is possible to accurately extract the model image Imo having similar characteristics to the subject image Ik and to accurately determine the body thickness distribution.

In the second embodiment, for a series of processes in S13 to S15 and a series of processes in S16 to S18, the processes in S16 to S18 may be performed first and then the processes in S13 to S15 may be performed. In addition, a series of processes in S13 to S15 or a series of processes in S16 to S18 may be omitted.

In each of the above-described embodiments, the image analysis device 30 may not include the position alignment unit and may not perform the alignment process. In addition, the image analysis device 30 may not include the scattered X-ray information acquisition unit 35 and the scattered X-ray removal unit 36 and may not perform the scattered X-ray information acquisition process and the scattered X-ray removal process. In this case, it is considered that the determined body thickness distribution is output to another device and the device performs various types of image processing or a radiography condition determination process using the received body thickness distribution. In addition, the image analysis device 30 may not perform the process of creating the body thickness distribution Tmi of the model image Mi and the image analysis device 30 may acquire the body thickness distribution Tmi created by another device.

The invention is not limited to each of the above-described embodiments and the body thickness distribution of the model image may be acquired by any method as long as it indicates the body thickness distribution of a model.

When the process (see S02 to S07 in FIG. 3 and S12 to S23 in FIG. 4) of determining the body thickness distribution of the subject image according to the invention is performed after the subject image is acquired and other desired image processing, such as the scattered X-ray removal process, is performed, using the determined body thickness distribution of the subject image, to generate a processed image, it is preferable to minimize the time from the acquisition of the subject image to the display of the processed image (the time from the acquisition of the subject image to the display of the processed image obtained by the process of determining the body thickness distribution of the subject image and other desired image processing such as the scattered X-ray removal process for the subject image).

For this purpose, in the image analysis device according to the invention, the image acquisition unit 31 may reduce the subject image to a predetermined size to generate a reduced image and acquire the reduced image, the model information acquisition unit 32 may acquire model information having a model image with a size corresponding to the reduced image, and the body thickness distribution determination unit 34 may specify a model image having characteristic information similar to the characteristic information of the reduced image, determine the body thickness distribution associated with the specified model image as the body thickness distribution of the reduced image, enlarge the determined body thickness distribution of the reduced image to the size of a desired subject image, and use the enlarged body thickness distribution as the body thickness distribution of the subject image. In this case, the processing load of the process of determining the body thickness distribution of the subject image (in particular, the process of acquiring the characteristic information of the reduced image and/or the process of specifying the model image having characteristic information similar to the characteristic information of the reduced image) and the processing time are likely to be reduced. In addition, the time from the acquisition of the subject image to the display of the processed image is reduced and the waiting time of the user is reduced. Therefore, it is possible to assist the efficient observation operation of the user. In addition, the above-mentioned effect is very large and it is possible to significantly reduce the operation time of the user in a situation in which, in medical facilities, a plurality of subject images of a plurality of subjects obtained by radiography are acquired, desired image processing, such as the process of determining the body thickness distribution of the subject image and the scattered X-ray removal process according to each of the above-described embodiments, is sequentially performed for each of the radiographic images of the plurality of subjects, and the obtained processed images are sequentially displayed such that the user observes the processed images. In addition, it is preferable to minimize the resolution of the reduced image in the range in which a resolution capable of appropriately determining similarity using the characteristic information acquired from the reduced image and the characteristic information of the model image is maintained. For example, a method is considered which sets an optimum size in advance for each part or on the basis of the size of the organ whose radiographic image will be analyzed.

For example, in the case in which, in medical facilities, a plurality of subject images of a plurality of subjects obtained by radiography are acquired, desired image processing, such as the process (for example, see S02 to S07 in FIG. 3 and S12 to S23 in FIG. 4 in each of the above-described embodiments) of determining the body thickness distribution of the subject image and the scattered X-ray removal process according to the invention, is sequentially performed for each of the radiographic images of the plurality of subjects, and the obtained processed images are sequentially displayed such that the user observes the processed images, it is preferable to effectively use the time from the acquisition of the subject image to the display of the processed image. For example, it is considered that reference information for image observation is displayed before the display of the processed image for the time from the acquisition of the subject image to the display of the processed image according to each of the above-described embodiments.

For example, as a third embodiment which is a modification of the image analysis device according to the first embodiment, after a subject image is acquired, for the period of time over which a series of processes (S02 to S07 in FIG. 3) for determining the body thickness distribution Tk of the subject image Ik is performed, some or all of the following processes may be performed: the scattered X-ray information acquisition unit 35 acquires the scattered X-ray information of the subject image using a predetermined temporary body thickness distribution; and the scattered X-ray removal unit 36 performs the scattered X-ray removal process for the subject image Ik, on the basis of the scattered X-ray information acquired using the temporary body thickness distribution, to generate a temporary processed image and displays the temporary processed image on the display unit 40 (temporary processed image generation and display process).

Figure 5:
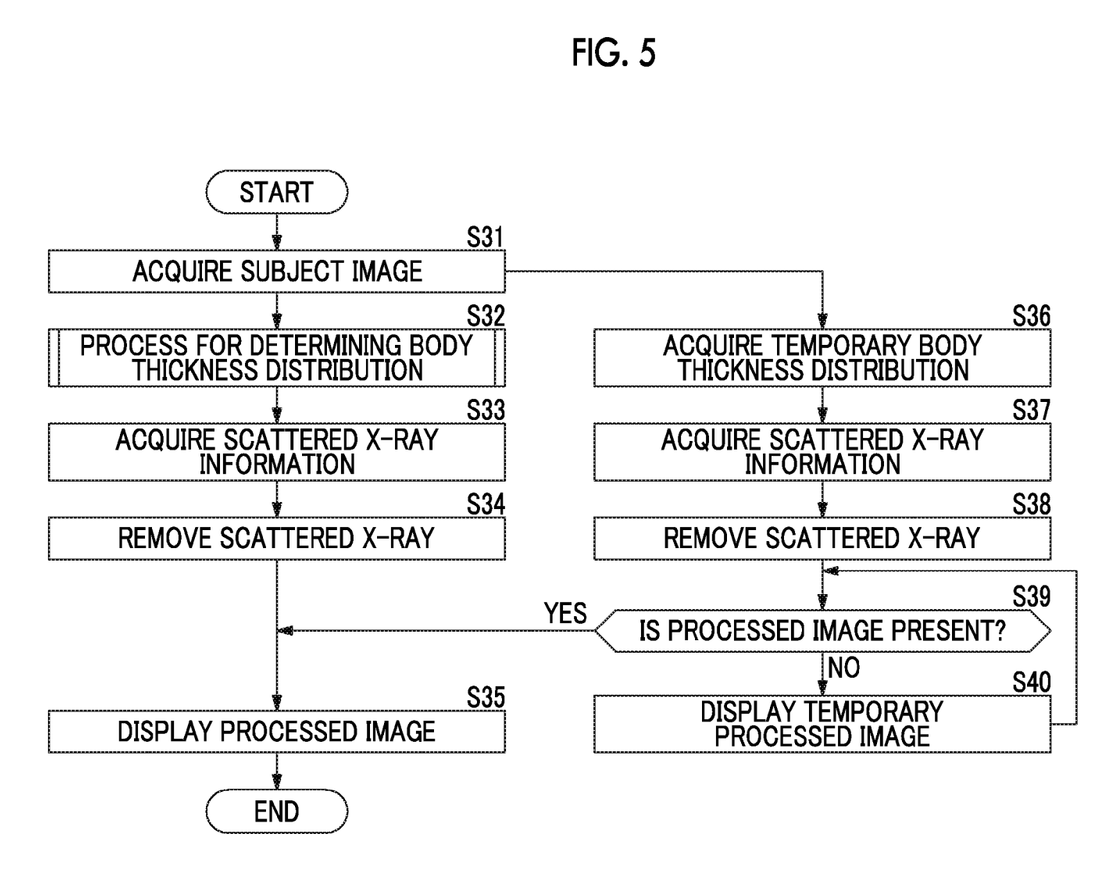
FIG. 5 is a flowchart illustrating a process performed in a third embodiment.

FIG. 5 is a flowchart illustrating the third embodiment. An image analysis device according to the third embodiment differs from the image analysis device according to the first embodiment in that, for the period of time over which a series of processes (S02 to S07 in FIG. 3) for determining the body thickness distribution Tk of the subject image Ik is performed, the scattered X-ray information acquisition unit 35 acquires scattered X-ray information indicating scattered X-rays included in the subject image Ik on the basis of a predetermined temporary body thickness distribution and the scattered X-ray removal unit 36 performs the scattered X-ray removal process for the subject image, on the basis of the scattered X-ray information acquired using the temporary body thickness distribution, to generate a temporary processed image and displays the temporary processed image on the display unit 40. For the other portions, the image analysis device according to the third embodiment includes the same components as the image analysis device 30 illustrated in FIG. 1 and the functions and processes of each component are substantially the same as those in the first embodiment. Therefore, the description is focused on the difference from the first embodiment and the description of the same portions will not be repeated.

In the third embodiment, as illustrated in FIG. 5, the image acquisition unit 31 acquires the subject image Ik, similarly to S01 in the first embodiment (S31), performs a process (S32) of determining the body thickness distribution Tk of the subject image Ik, similarly to the first embodiment (S02 to S07 in FIG. 3), acquires the scattered X-ray information (the primary X-ray image Ip and the scattered X-ray image Is), using the determined body thickness distribution Tk, on the basis of Conditional Expressions (1) and (2), similarly to the optional example of the first embodiment (S33), and subtracts the acquired scattered X-ray image Is from the subject image Ik to perform the scattered X-ray removal process (S34), similarly to the optional example of the first embodiment.

In the third embodiment, when the image acquisition unit 31 acquires the subject image (S31), the scattered X-ray information acquisition unit 35 acquires a predetermined temporary body thickness distribution in parallel to the process in S32 (S36), acquires the scattered X-ray information (the primary X-ray image Ip and the scattered X-ray image Is), using the acquired temporary body thickness distribution, on the basis of Conditional Expressions (1) and (2), similarly to the optional example of the first embodiment (S37), subtracts a scattered X-ray image Is' which is acquired using the temporary body thickness distribution from the subject image Ik, on the basis of the scattered X-ray image Is', to generate a temporary processed image from which the influence of the scattered X-rays has been removed, similarly to the optional example of the first embodiment, and stores the temporary processed image in the storage unit 42 (S38). Then, the image analysis device 30 determines whether or not the processed image obtained by the process in S34 has been generated. When the processed image has not been generated (S39, No), the image analysis device 30 displays the temporary processed image on the display unit 40 until the processed image is generated (S39, Yes) (S40). On the other hand, when the processed image obtained by the process in S34 has been generated (S39, Yes), the image analysis device displays the processed image on the display unit 40 (S35).

According to the third embodiment, in the radiographic image analysis device which acquires the subject image Ik, performs the process of determining the body thickness distribution Tk of the subject image Ik, performs desired image processing, such as the scattered X-ray removal process, and displays the obtained processed image, for the period of time over which a series of processes for determining the body thickness distribution Tk of the subject image Ik is performed, some or all of the following processes are performed: desired image processing, such as a process of removing the scattered X-rays of the subject image, is performed using the predetermined temporary body thickness distribution; the processed image which is obtained using the temporary body thickness distribution is generated as the temporary processed image; and the temporary processed image is displayed on the display unit 40. Therefore, the user can effectively use the time until the processed image is displayed and observe the temporary processed image obtained using the temporary body thickness distribution to roughly check the region of interest in the subject image or whether the radiograph conditions applied to the subject image are correct. Therefore, the user can effectively perform observation and it is possible to provide reference information for the user's observation.

In the third embodiment, the "predetermined body thickness distribution" may be any body thickness distribution which substantially corresponds to the subject K. For example, among the body thickness distributions which are obtained from a plurality of previous subject images by the body thickness determination process according to each of the above-described embodiments, the latest body thickness distribution can be used. In addition, the body thickness distribution of a standard subject may be used. In addition, a series of processes (S32) for determining the body thickness distribution of the subject image Ik in the third embodiment may be any process for determining the body thickness distribution Tk of the subject K as long as it includes at least the following processes: a model information acquisition process of acquiring model information in which a model image captured by irradiating each of a plurality of models different from at least the subject with radiation is associated with the body thickness distribution of the model in the model image, for each of the plurality of models; and a body thickness distribution determination process (a body thickness distribution determination process according to the invention) of acquiring characteristic information indicating the characteristics of the subject image, acquiring characteristic information indicating the characteristics of each of a plurality of model images on the basis of a plurality of model information items, specifying the model image having characteristic information similar to the characteristic information of the subject image, and determining a body thickness distribution associated with the specified model image as the body thickness distribution of the subject image. For example, a series of processes (S32) for determining the body thickness distribution may be a process (a process corresponding to S12 to S23 in FIG. 4) according to the second embodiment or the alignment process may be omitted. In the third embodiment, the process (S33, S34, S37, and S38) of removing the scattered X-rays from the subject image Ik has been described. However, the invention is not limited thereto. Image processing other than the scattered X-ray removal process may be performed for the subject image Ik, or the scattered X-ray removal process and other types of image processing may be performed for the subject image Ik. The process from S36 to S38 can be performed for any period which partially or entirely overlaps the period of the process in S32 and it is preferable to early perform the process from S36 to S38 after the subject image Ik is acquired, in order to rapidly display the temporary processed image and to rapidly provide reference information for the user's observation.

The invention is not limited to the above-described embodiments and the body thickness distribution obtained by the invention can be used in any process for determining image processing conditions corresponding to the body thickness of the subject for the subject image. For example, it is considered that the body thickness distribution obtained by the invention is used in, for example, a gradation process of adjusting concentration or contrast, a noise suppressing process, a dynamic range adjustment process, and a frequency emphasis process for the subject image which is a still image or a moving image. In addition, the body thickness distribution obtained by the invention can be used in any process for determining radiography conditions corresponding to the body thickness for the subject image. When the body thickness distribution obtained by the invention is used to determine each image processing condition or radiography conditions, an accurate body thickness distribution is applied to the subject image and it is possible to increase the effect of improving image quality using the determined image processing conditions or radiography conditions.

For example, in an energy subtraction technique which acquires a radiographic image using the difference between two radiographic images acquired by capturing high-energy and low-energy radiations while changing the tube voltage, a process may be performed which determines a weight coefficient such that a large weight is given to a high-energy image at the position where the body thickness is large when a low-energy image is subtracted from the high-energy image according to the body thickness distribution of the subject obtained by the invention. In this case, since an accurate body thickness distribution is applied to the subject image, it is possible to reduce the influence of a beam hardening phenomenon in which the quality of radiation varies depending on the thickness of the subject and to appropriately improve the quality of the processed image.

In the field of a radiolucent image application technique or a technique for capturing the image of the same subject a plurality of times to acquire a plurality of radiographic images, such as a tomosynthesis technique or a moving image capture technique, it is preferable that the body thickness distribution of the subject is acquired from the subject image which is captured first by the method according to the invention and the radiography conditions of the subject whose image is to be captured are determined on the basis of the acquired body thickness distribution. The subsequent subject image can be captured under appropriate radiography conditions corresponding to the body thickness. Therefore, it is possible to improve the quality of the subsequent subject image so as to be suitable for diagnosis.

It is preferable to store dose management information in which the body thickness distribution of the subject obtained by the invention is associated with the radiography conditions for each subject. The radiography conditions may include a set value which is set in, for example, the X-ray source or exposure time or may include a measured value, such as a dose that is actually radiated, which is measured by, for example, a detector and exposure time. A plurality of dose management information items about the subject are acquired as dose history information for each subject and the cumulative exposure of the subject at each position for a predetermined period of time is calculated on the basis of the dose history information. In this way, it is possible to provide useful information which is a dose management index for each region indicating whether the cumulative exposure is equal to or greater than a predetermined threshold value and is beyond an allowable range in a predetermined region such as a predetermined organ. In addition, dose management information about each of a plurality of different subjects can be acquired and statistical analysis can be performed to specify which of the radiography conditions is used according to the tendency of the body thickness distribution. It is possible to provide reference information for determining the radiography conditions of a new subject or for estimating the radiography conditions of the previous subject.

When two subject images forming a stereoscopic image are selected from a plurality of subject images captured by a tomosynthesis device, preferably, the body thickness distribution of the subject obtained by the invention is acquired and two subject images are selected such that an appropriate amount of parallax or an appropriate convergence angle (an angle formed between the imaging directions of two subject images forming the stereoscopic image) is obtained according to the acquired body thickness distribution. For example, the following process can be performed: an index value indicating the characteristics of the body thickness distribution, such as a maximum value, a mean, or a median, is extracted from the body thickness distribution of the subject; parallax determination information which is associated with an appropriate amount of parallax (or an appropriate convergence angle) such that the amount of parallax (or the convergence angle) increases as the body thickness of the subject increases is created for each range of the index value and then acquired; the amount of parallax (or the convergence angle) corresponding to the index value extracted from the body thickness distribution of the subject is determined as the amount of parallax (or the convergence angle) of the stereoscopic image, on the basis of the parallax determination information; and two subject images having the amount of parallax (or the convergence angle) therebetween are selected as the subject images forming the stereoscopic image. For example, the following process can be performed: an index value indicating the characteristics of the body thickness distribution is calculated according to the body thickness distribution of the subject; the subjects are classified into a plurality of body types, such as a thin body type, a standard body type, and a thick body type, by the index value; the amount of parallax (or the convergence angle) corresponding to the divided classification is determined as the amount of parallax of the stereoscopic image of the subject; and two subject images having the amount of parallax therebetween are selected as the subject images forming the stereoscopic image. As such, when two subject images forming the stereoscopic image are selected from a plurality of subject images, the body thickness distribution of the subject obtained by the invention is acquired and two subject images are appropriately selected according to the acquired body thickness distribution such that the amount of parallax or the convergence angle increases as the body thickness increases. In this case, it is possible generate a stereoscopic image with a quality suitable for observation according to the body thickness distribution. For the amount of parallax and the convergence angle, it is possible to refer to the previous patent applications filed by the inventors (for example, JP2013-198736A, JP2013-198508A, and JP2013-154165A).

Each of the above-described embodiments is illustrative and all of the descriptions should not be used to interpret the technical scope of the invention in a limited manner. The aspects of the invention are not limited to each of the above-described embodiments (the first to third embodiments, other modification examples, and application examples) and the invention includes any combination of the components according to each embodiment and various modifications which can be made by those skilled in the art. That is, various additions, changes, and partial deletions can be made, without departing from the conceptual idea and meaning of the invention which are derived from content defined in the claims and equivalents thereof.

In addition, for example, the system configuration, the hardware configuration, the process flow, the module configuration, the user interface, and the specific content of processing can be modified in various ways without departing from the scope and spirit of the invention and these modifications are also included in the technical scope of the invention. For example, some or all of the components of the image analysis device may be implemented by a single workstation or may be implemented by one or more workstations, servers, and the storage devices which are connected to each other through a network.

In the above-described embodiments, the scattered X-ray removal process is performed using the radiographic image acquired by the imaging device 10 which captures the radiographic image of the subject using the radiation detector 14. However, the invention can be applied to the structures disclosed in JP1996-266529A (JP-H08-266529A) and JP1997-24039A (JP-H09-24039A) in which the radiographic image information of the subject is stored and recorded on a storage phosphor sheet as a radiation detector and the radiographic image is photoelectrically read from the storage phosphor sheet and is then used.

What is claimed is:

1. A radiographic image analysis device that analyzes a subject image captured by irradiating a subject with radiation to estimate a body thickness distribution of the subject, the device comprising:
    an image acquisition unit that acquires the subject image;
    a model information acquisition unit that acquires model information, in which a model image captured by irradiating each of a plurality of models different from the subject with radiation is associated with a body thickness distribution of the model in the model image, for each of the plurality of models; and
    a body thickness distribution determination unit that acquires characteristic information indicating characteristics of the subject image, acquires characteristic information indicating the characteristics of each of the plurality of model images, on the basis of the plurality of model information items, specifies the model image having characteristic information similar to the characteristic information of the subject image, and determines the body thickness distribution associated with the specified model image as the body thickness distribution of the subject image,
    wherein the image acquisition unit further acquires grid information including information indicating whether a scattered X-ray removal grid is used to capture the subject image and the type of scattered X-ray removal grid when the scattered X-ray removal grid is used to capture the subject image,
    the model information acquisition unit further acquires the grid information of the model image, and
    the body thickness distribution determination unit acquires the characteristic information from the subject image and the model image included in the model information having grid information identical to the grid information of the subject image and specifies the model image having characteristic information similar to the characteristic information of the subject image.

2. The radiographic image analysis device according to claim 1,
    wherein the characteristic information is imaging target information indicating physical characteristics of an imaging target.

3. The radiographic image analysis device according to claim 1, further comprising:
    a position alignment unit that aligns the subject image and the model image such that the corresponding positions of the subject image and the model image are aligned with each other,
    wherein the body thickness distribution determination unit acquires the characteristic information from the subject image and the model image which are aligned with each other and specifies the model image having characteristic information similar to the characteristic information of the subject image.

4. The radiographic image analysis device according to claim 1,
    wherein the subject image is captured without using the scattered X-ray removal grid.

5. The radiographic image analysis device according to claim 4,
    wherein the model image is captured without using the scattered X-ray removal grid.

6. The radiographic image analysis device according to claim 1,
    wherein the body thickness distribution of the model image is created by acquiring a three-dimensional image of the model obtained by three-dimensional imaging and measuring a body thickness on a straight line corresponding to a radiation path of the model image at each position of the acquired three-dimensional image.

7. The radiographic image analysis device according to claim 1,
    wherein the image acquisition unit further acquires part information indicating an imaging target part of the subject image,
    the model information acquisition unit further acquires the part information of the model image, and
    the body thickness distribution determination unit acquires the characteristic information from the subject image and the model image included in the model information having part information identical to the part information of the subject image and specifies the model image having characteristic information similar to the characteristic information of the subject image.

8. A radiographic image analysis method that is performed in a radiographic image analysis device and analyzes a subject image captured by irradiating a subject with radiation to estimate a body thickness distribution of the subject, comprising:
    an image acquisition step of acquiring the subject image;
    a model information acquisition step of acquiring model information, in which a model image captured by irradiating each of a plurality of models different from the subject with radiation is associated with a body thickness distribution of the model in the model image, for each of the plurality of models; and
    a body thickness distribution determination step of acquiring characteristic information indicating characteristics of the subject image, acquiring characteristic information indicating the characteristics of each of the plurality of model images, on the basis of the plurality of model information items, specifying the model image having characteristic information similar to the characteristic information of the subject image, and determining the body thickness distribution associated with the specified model image as the body thickness distribution of the subject image,
    wherein the image acquisition step further acquires grid information including information indicating whether a scattered X-ray removal grid is used to capture the subject image and the type of scattered X-ray removal grid when the scattered X-ray removal grid is used to capture the subject image,
    the model information acquisition step further acquires the grid information of the model image, and
    the body thickness distribution determination step acquires the characteristic information from the subject image and the model image included in the model information having grid information identical to the grid information of the subject image and specifies the model image having characteristic information similar to the characteristic information of the subject image.

9. A non-transitory computer readable recording medium having recorded therein a radiographic image analysis program that analyzes a subject image captured by irradiating a subject with radiation to estimate a body thickness distribution of the subject and causes a computer to perform:
an image acquisition step of acquiring the subject image;
a model information acquisition step of acquiring model information, in which a model image captured by irradiating each of a plurality of models different from the subject with radiation is associated with a body thickness distribution of the model in the model image, for each of the plurality of models; and
a body thickness distribution determination step of acquiring characteristic information indicating characteristics of the subject image, acquiring characteristic information indicating the characteristics of each of the plurality of model images, on the basis of the plurality of model information items, specifying the model image having characteristic information similar to the characteristic information of the subject image, and determining the body thickness distribution associated with the specified model image as the body thickness distribution of the subject image,
wherein the image acquisition step further acquires grid information including information indicating whether a scattered X-ray removal grid is used to capture the subject image and the type of scattered X-ray removal grid when the scattered X-ray removal grid is used to capture the subject image,
the model information acquisition step further acquires the grid information of the model image, and
the body thickness distribution determination step acquires the characteristic information from the subject image and the model image included in the model information having grid information identical to the grid information of the subject image and specifies the model image having characteristic information similar to the characteristic information of the subject image.

10. A radiographic image analysis device that analyzes a subject image captured by irradiating a subject with radiation to estimate a body thickness distribution of the subject, the device comprising:
an image acquisition unit that acquires the subject image;
a model information acquisition unit that acquires model information, in which a model image captured by irradiating each of a plurality of models different from the subject with radiation is associated with a body thickness distribution of the model in the model image, for each of the plurality of models; and
a body thickness distribution determination unit that acquires characteristic information indicating characteristics of the subject image, acquires characteristic information indicating the characteristics of each of the plurality of model images, on the basis of the plurality of model information items, specifies the model image having characteristic information similar to the characteristic information of the subject image, and determines the body thickness distribution associated with the specified model image as the body thickness distribution of the subject image,
wherein the body thickness distribution of the model image is created by acquiring a three-dimensional image of the model obtained by three-dimensional imaging and measuring a body thickness on a straight line corresponding to a radiation path of the model image at each position of the acquired three-dimensional image.

11. A radiographic image analysis method that is performed in a radiographic image analysis device and analyzes a subject image captured by irradiating a subject with radiation to estimate a body thickness distribution of the subject, comprising:
an image acquisition step of acquiring the subject image;
a model information acquisition step of acquiring model information, in which a model image captured by irradiating each of a plurality of models different from the subject with radiation is associated with a body thickness distribution of the model in the model image, for each of the plurality of models; and
a body thickness distribution determination step of acquiring characteristic information indicating characteristics of the subject image, acquiring characteristic information indicating the characteristics of each of the plurality of model images, on the basis of the plurality of model information items, specifying the model image having characteristic information similar to the characteristic information of the subject image, and determining the body thickness distribution associated with the specified model image as the body thickness distribution of the subject image,
wherein the body thickness distribution of the model image is created by acquiring a three-dimensional image of the model obtained by three-dimensional imaging and measuring a body thickness on a straight line corresponding to a radiation path of the model image at each position of the acquired three-dimensional image.

12. A non-transitory computer readable recording medium having recorded therein a radiographic image analysis program that analyzes a subject image captured by irradiating a subject with radiation to estimate a body thickness distribution of the subject and causes a computer to perform:
an image acquisition step of acquiring the subject image;
a model information acquisition step of acquiring model information, in which a model image captured by irradiating each of a plurality of models different from the subject with radiation is associated with a body thickness distribution of the model in the model image, for each of the plurality of models; and
a body thickness distribution determination step of acquiring characteristic information indicating characteristics of the subject image, acquiring characteristic information indicating the characteristics of each of the plurality of model images, on the basis of the plurality of model information items, specifying the model image having characteristic information similar to the characteristic information of the subject image, and determining the body thickness distribution associated with the specified model image as the body thickness distribution of the subject image,
wherein the body thickness distribution of the model image is created by acquiring a three-dimensional image of the model obtained by three-dimensional imaging and measuring a body thickness on a straight line corresponding to a radiation path of the model image at each position of the acquired three-dimensional image.

* * * * *